US009956374B2

(12) United States Patent
Hoefler

(10) Patent No.: US 9,956,374 B2
(45) Date of Patent: May 1, 2018

(54) ISOLATION FLOATATION CHAMBER

(71) Applicant: Craig Hoefler, Venice, CA (US)

(72) Inventor: Craig Hoefler, Venice, CA (US)

( * ) Notice: Subject to any disclaimer, the term of this patent is extended or adjusted under 35 U.S.C. 154(b) by 604 days.

(21) Appl. No.: 14/265,336

(22) Filed: Apr. 29, 2014

(65) Prior Publication Data

US 2015/0306341 A1 Oct. 29, 2015

Related U.S. Application Data

(60) Provisional application No. 61/817,373, filed on Apr. 30, 2013.

(51) Int. Cl.
*A61M 21/00* (2006.01)
*A61L 2/18* (2006.01)
*A61L 2/10* (2006.01)
*A61L 2/00* (2006.01)
*A61L 9/00* (2006.01)
*A61M 21/02* (2006.01)

(52) U.S. Cl.
CPC .......... *A61M 21/0094* (2013.01); *A61L 2/00* (2013.01); *A61L 2/10* (2013.01); *A61L 2/183* (2013.01); *A61L 9/00* (2013.01); *A61M 21/02* (2013.01); *A61M 2021/0022* (2013.01); *A61M 2021/0066* (2013.01); *A61M 2205/11* (2013.01); *A61M 2205/3368* (2013.01); *A61M 2209/10* (2013.01)

(58) Field of Classification Search
CPC ........ C02F 2303/04; C02F 1/001; C02F 1/78; C02F 2103/42; A61G 10/005; A61G 10/02; A61H 2033/048
See application file for complete search history.

(56) References Cited

U.S. PATENT DOCUMENTS

| | | | | |
|---|---|---|---|---|
| 5,635,059 | A * | 6/1997 | Johnson | C02F 1/46 204/293 |
| 5,652,972 | A * | 8/1997 | Chartrand | E04H 4/0043 219/535 |
| 7,578,783 | B2 | 8/2009 | Klein | |
| 2002/0122525 | A1* | 9/2002 | Rosenberger | G21C 19/07 376/272 |

(Continued)

*Primary Examiner* — Christine H Matthews
(74) *Attorney, Agent, or Firm* — William J. Benman; Benman, Brown & Williams

(57) ABSTRACT

An isolation chamber and disinfection system. The novel system includes an enclosure for providing a sturdy, lightless and soundproofed environment and for containing a solution for supporting a user in a state of floatation; a disinfection system for disinfecting the solution, the disinfection system including an ultraviolet disinfection system and an ozone injection system; and a pump for removing the solution from the enclosure and circulating it through the disinfection system at a predetermined flow rate. The enclosure is formed from interlocking, foam-insulated panels and lined with a potable liner that holds the solution. In relationship to the isolation chamber, in accordance with the present teachings, an improved method of disinfection is taught using UV radiation with ozone injection. Ozone has a short half-life and leaves substantially no toxic byproducts. Verification of disinfection can be accomplished by monitoring the dissolved ozone, which can be determined accurately utilizing a dissolved ozone sensor system.

17 Claims, 3 Drawing Sheets

12
98
100
AIR VENT IN
AIR VENT OUT
24
PROCESSED SOLUTION RETURNED INTO CHAMBER
16
22
54
54
18
18
40

(56) References Cited

U.S. PATENT DOCUMENTS

| | | | | |
|---|---|---|---|---|
| 2004/0025249 | A1* | 2/2004 | Berry | A61H 33/6073 4/695 |
| 2006/0020159 | A1* | 1/2006 | Ellen | A47C 21/08 600/21 |
| 2007/0108056 | A1* | 5/2007 | Nyberg | B01D 61/44 204/554 |
| 2010/0176520 | A1* | 7/2010 | Cunningham | A01K 13/001 261/121.1 |
| 2010/0200517 | A1* | 8/2010 | Harris | C02F 1/001 210/760 |
| 2010/0281609 | A1* | 11/2010 | Holmgren | E04H 4/10 4/498 |
| 2014/0166498 | A1* | 6/2014 | Orolin | C02F 1/4672 205/743 |
| 2014/0238913 | A1* | 8/2014 | Hoang | E04H 4/129 210/167.12 |
| 2015/0087893 | A1* | 3/2015 | Hill | A61M 21/0094 600/26 |

* cited by examiner

ISOLATION FLOATATION CHAMBER

REFERENCE TO RELATED APPLICATION

This application claims priority from a Provisional Application entitled Isolation Floatation Chamber, filed Apr. 30, 2013, by C. Hoefler, application No. 61/817,373.

BACKGROUND OF THE INVENTION

Field of the Invention

The present invention relates to isolation chambers. More specifically, the present invention relates to systems and methods for disinfecting floatation tanks.

Description of the Related Art

An isolation chamber, or floatation tank, is a dark, soundproofed enclosure containing a layer of salt water upon which a user floats, typically for relaxation or meditation purposes. The chamber is designed to isolate the user from external stimuli such as light, sound, smell, and, in particular, gravity. Epsom salt is usually added to the water in the isolation tank to increase the density of the solution such that the user floats comfortably near the surface with the face above the water. The buoyancy created by this salt solution effectively eliminates the body's specific gravity, bringing the floater close to an experience of total weightlessness.

Isolation chambers for commercial usage must maintain proper sanitation practices to ensure a safe and healthy environment for the users. As with swimming pools and other recreational water facilities, the water in an isolation chamber is subject to undesirable contaminants introduced by the users and environment. These contaminants may include pathogenic micro-organisms such as viruses, bacteria, protozoa, and fungi. Commercial isolation chambers should therefore include a properly designed disinfection system for killing these micro-organisms to prevent the transmission of infectious diseases.

Conventional isolation chambers typically rely on chemical disinfectants such as chlorine for water sanitation. Chlorine disinfection is inexpensive, quick and effective at killing most pathogenic microbes, and leaves a residual in the water that continues disinfecting for a long period of time. Residual chlorine is desirable, and often required, for public swimming pools and similar venues where a user may be exposed to contaminants introduced by other swimmers. This residual is used to validate a certain level of decontamination. This criteria is designed to be used with regular water in an open space.

In a magnesium sulfate solution one cannot accurately monitor the chemical residual, making it impossible for either the operator or public health authority to determine correct measurement of disinfecting chemicals, resulting in blind dosing.

Chemical disinfectants react with organic matter to produce toxic disinfection by-products such as trihalomethanes, haloacetic acids, chlorite, and others. In particular, chlorine reacts with ammonia or nitrogen containing compounds such as sweat, saliva, and urine to produce chloramines. Exposure to chloramines can cause respiratory problems, rashes and other skin conditions, eye irritation, digestive disorders, and other health issues. In addition, chloramines also produce an irritating odor which is particularly undesirable for isolation chambers, where the desired goal is to isolate the user as much as possible from external stimuli.

Hence, a need exists in the art for an improved system or method for sanitizing and monitoring isolation chambers that is safer than conventional chemical approaches.

SUMMARY OF THE INVENTION

The need in the art is addressed by the isolation system of the present invention. The novel system includes an enclosure for providing a lightless and soundproofed environment and for containing a solution for supporting a user in a state of floatation; a disinfection system for disinfecting the solution, the disinfection system including an ultraviolet disinfection system and an ozone injection system; and a pump for removing the solution from the enclosure and circulating it through the disinfection system at a predetermined flow rate. In an illustrative embodiment, the disinfection system includes a multi-stage filtration system with a 10 micron pre-filter, a 5 micron pre-filter, and a 0.5 micron filter; a 150 Watt medium-pressure ultraviolet lamp; a 4 grams/hr ozone generator; and a pump for providing a flow-rate of about 90 gallons per minute. The enclosure is formed from interlocking, foam-insulated panels and lined with a potable liner that holds the solution.

In relationship to the isolation chamber, in accordance with the present teachings, an improved method of disinfection is taught using UV radiation with ozone injection. Ozone has a short half-life and leaves substantially no toxic byproducts. Verification of disinfection can be accomplished by monitoring the dissolved ozone, which can be determined accurately utilizing a dissolved ozone sensor system.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

The present invention provides a novel isolation chamber and disinfection system designed for commercial usage. Unlike conventional isolation tanks, the inventive system does not rely on chemical disinfectants. Instead, it uses a combination of UV (ultraviolet) radiation and ozone to disinfect the floatation solution. In accordance with the present teachings, the solution is disinfected between each and every use. Thus, there is no need for a residual disinfect (that continues disinfecting during operation) since there is no cross-contamination between users. The only contaminants that a user would be exposed to are the contaminants brought into the chamber by the user himself, and any contaminants remaining in the solution after the disinfection process. The system is therefore designed to thoroughly kill pathogens and break down organic compounds in the solution without producing any harmful by-products, leaving a pure, clean, and safe environment for the next user.

Figure 1:
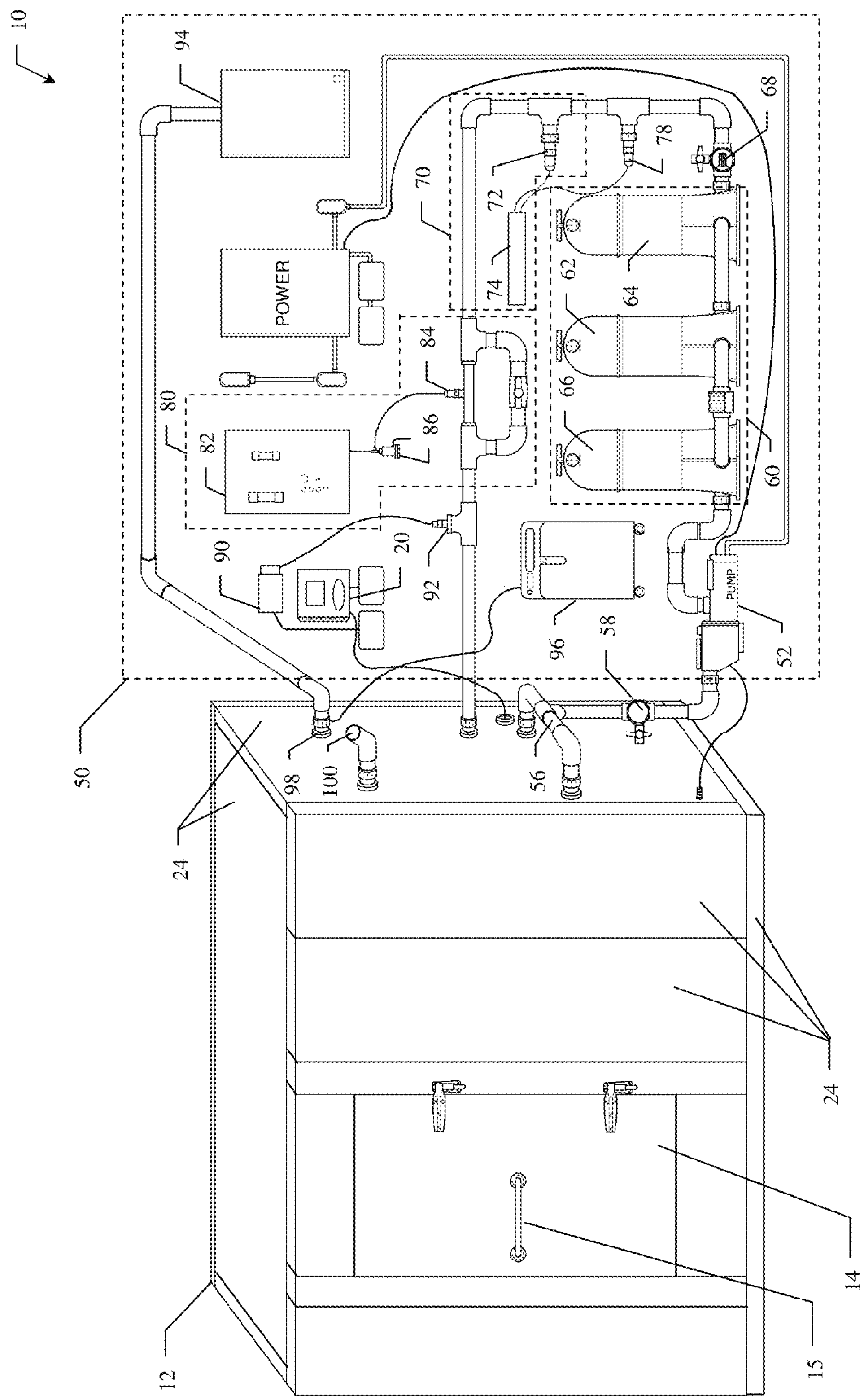
FIG. 1 is a simplified diagram of an isolation system designed in accordance with an illustrative embodiment of the present invention.
Figure 2:
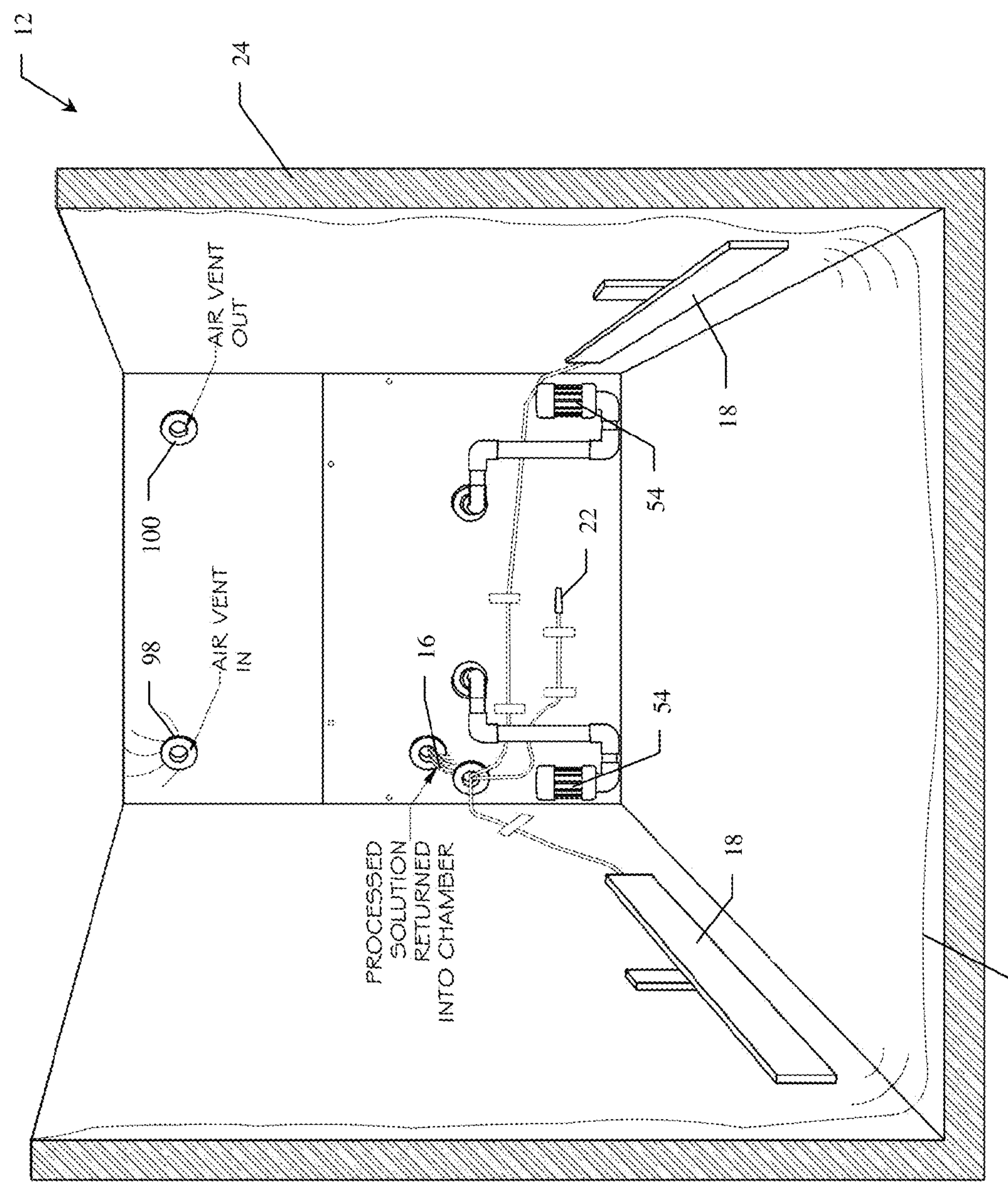
FIG. 2 is a simplified diagram of an interior of an isolation chamber designed in accordance with an illustrative embodiment of the present invention.

FIG. 1 is a simplified diagram showing an external view of an isolation system 10 designed in accordance with an illustrative embodiment of the present invention, while FIG. 2 shows an interior view of the isolation chamber 12. As shown in FIGS. 1 and 2, the isolation system 10 includes an isolation chamber 12, which is a lightless, soundproofed enclosure designed to provide a light- and sound-free environment therein. A door 14 provides access to the chamber 12. The chamber 12 contains a solution 16 having a specific gravity of about 1.25 to 1.3 for supporting a user in a state of floatation. In the illustrative embodiment, the chamber 12 contains a 12 inch deep, saturated solution 16 of 1000 lbs of USP grade magnesium sulfate (Epsom salt) in about 250 gallons of water. The chamber 12 includes heating pads 18 coupled to a heater controller 20 and sensor 22 for maintaining the temperature of the solution to match skin temperature (approximately 95°). The user floats in the chamber 12 in a dark, silent environment, with a feeling of weightlessness.

Figure 3:
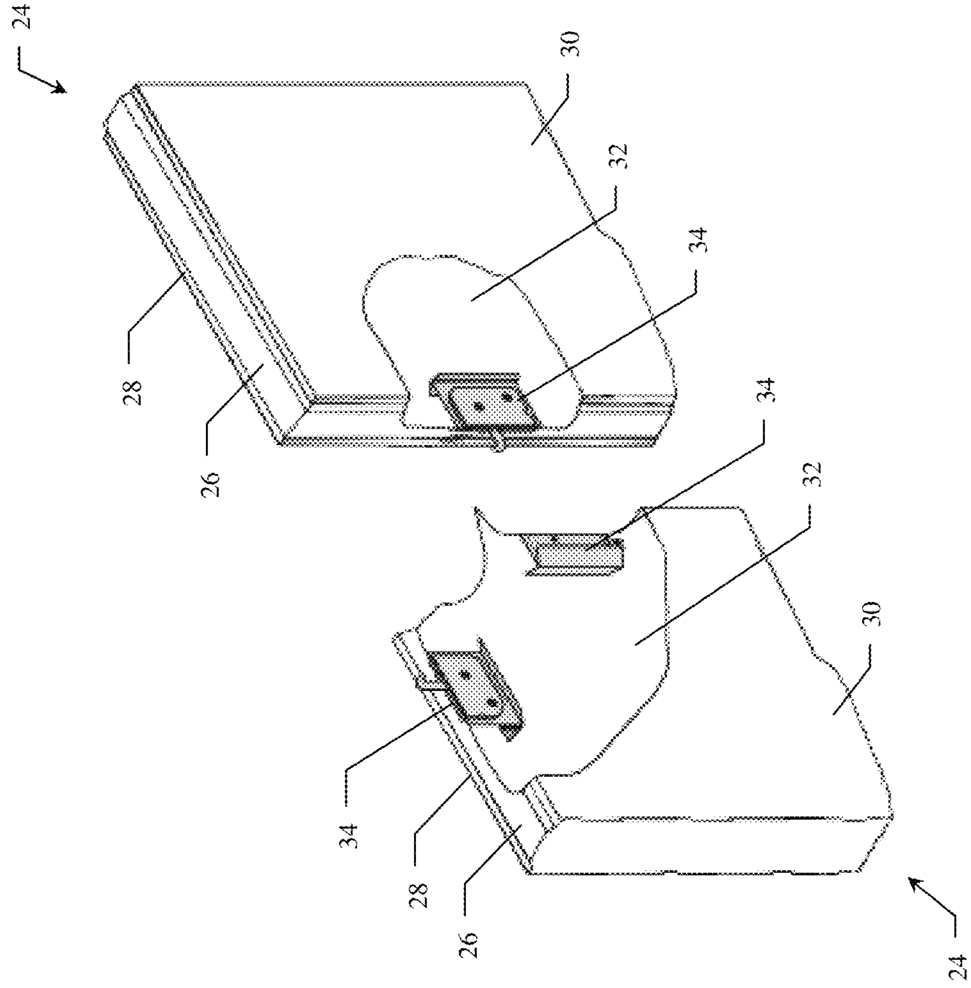
FIG. 3 is a simplified diagram showing a cut-out view of two insulated panels designed in accordance with an illustrative embodiment of the present invention.

In the preferred embodiment, the chamber 12 is formed from interlocking insulated panels 24. FIG. 3 shows a cut-out view of two insulated panels 24 designed in accordance with an illustrative embodiment of the present teachings. Each panel 24 includes a 3.5" thick wood frame 26 with an exterior skin 28 and interior skin 30. In the illustrative embodiment, the skins 28 and 30 are made from aluminum, stainless steel, or other anodized metal. The interior of the panel 24 is filled with injected foam insulation 32 such as polyurethane or polystyrene. The panels 24 also include steel cam locks 34 for securely attaching adjacent panels 24 together. Similar panels are commonly used for walk-in refrigeration units. These panels 24 are excellent for creating a sturdy, light-proof, sound resistant, and non-rusting enclosure for the isolation chamber 12 that can be easily assembled and dismantled.

The size of the chamber 12 should be sufficient for a single user to easily enter and exit as well as stand up and lay down inside (minimum 4 ft width, 8 ft length, and 7 ft height). For safety, the enclosure 12 should have a non-latching door 14 that pushes open easily from the inside (using, for example, magnetic gaskets). Ideally, the door 14 should seal flat on the outside so that the door 14 cannot be opened from the outside without the use of the exterior handle 15, which should be positioned horizontal at about 48" from the ground so that a child cannot enter the chamber 12 without help from an adult. The door 14 should be a minimum of 29" wide by 50" tall. Safety grab bars may be included inside the enclosure 12 for user assistance.

As shown in FIG. 2, the interior of the chamber 12 includes a liner 40 for containing the floatation solution 16. In the illustrative embodiment, the liner 40 is made from potable, non-toxic PVC, preferably at least 0.40 mil thick. The liner 40 can be custom made to fit the size and shape of the enclosure 12 and then attached to the panels 24 of the chamber 12 using hang tabs positioned along the top outer perimeter. The tabs are stapled into the rim prior to the placement of the ceiling panel to secure the liner 40 in position. In the preferred embodiment, the liner 40 fully encompasses the interior dimensions of the structure 12. A non-slip floor pad should be added on top of the liner 40 near the entry.

The heating pads 18 are attached using adhesive to the interior wall of the chamber 12 between the insulated panel 24 and the liner 40, at a height where the entire pad is below the water level. The user is therefore never in direct contact with the heaters 18, only with the non-toxic liner 40, the potable suction fittings 54 (shown in FIG. 2), and the purified solution 16.

As shown in FIG. 1, the isolation system 10 includes a novel disinfection system 50 located external to the chamber 12 for cleaning and disinfecting the solution 16 before each use. The disinfection system 50 includes a pump 52 for removing the solution 16 from the chamber 12, a filtration system 60 for removing larger particles from the solution 16, a UV disinfection system 70, and an ozone injection system 80.

In the illustrative embodiment, the pump 52 is a 1 hp high-head pump that circulates the solution 16 through the disinfection system 50 at a flow rate of about 90 gal/min. The flow rate must be compatible with the UV disinfection system 70. UV radiation is only effective at a certain flow rate. If the solution travels through the system 70 too quickly, it will not receive enough UV exposure to have an adequate kill factor. If the flow is too slow, however, heat may build up and damage the UV lamp 72.

The solution 16 is extracted from the chamber 12 by the pump 52 through two VGB compliant suction fittings 54 (shown in FIG. 2), located at least 36 inches apart. A 2" cross 56 is positioned directly in the center of the two suction fittings 54 to ensure that the pump 52 is pulling solution equally from both sides. Pulling the solution 16 from two locations safeguards that if someone is in the chamber 12 while the pump 52 is on, he will not be trapped by the suction and held underwater. Even though the disinfection system is not designed to be used when someone is in the chamber 12, the system 10 should still be VGA compliant for optimal safety.

In the preferred embodiment, the suction fittings 54 are 4" Schedule 80 PVC vertical slot suction fittings serve as turbulent water intakes. The vertical slot suction fittings 54 are used to effectively remove surface debris (such as hair, skin cells, micro-organisms, etc.) from the solution 16, each at a rate of about 50 gallons per minute. Each partially submerged vertical slot suction fitting 54 has eight ¼" wide vertical slots that run the elevation of the fitting permitting the solution 16 to be pulled from variable depths, from all around (360 degrees), and without pulling air into system. The vertical slot suction fittings 54 should be APSP-16 compliant.

In accordance with the present teachings, the filtration system 60 includes at least two filters: a pre-filter 62 with a 5 micron cartridge followed by a filter 64 with a 0.5 micron cartridge. In a preferred embodiment, the filtration system 60 also includes an additional pre-filter 66 with a 10 micron cartridge before the 5 micron pre-filter 62. The filtration system 60 therefore removes all particles larger than 0.5 microns from the solution 16. This is important since the presence of particles can reduce the effectiveness of the UV disinfection. Filter cartridges used for conventional pool filtration systems (typically 20 micron) are insufficient for this purpose. Cartridges rated at 5 micron and 0.5 micron can be custom made by a good filter manufacturer. In a preferred embodiment, the 2" cross 56 includes a 0.5" ball valve out of the top port that works as a pressure release so that the filters can be serviced without entering the chamber 12 to release the pressure by removing the suction fittings 54 at the 1.5" unions.

After filtration, the solution 16 goes through UV disinfection. In accordance with the present teachings, the UV disinfection system 70 includes a UV lamp 72 positioned to irradiate the solution 16 as it flows by. The UV lamp 72 should include a 150 W, medium-pressure (broad spectrum) germicidal UV bulb with a close proximity Schedule 80 housing. The system 70 also includes a UV ballast 74 for regulating the electrical current flow to the UV bulb 72. The ballast 74 minimizes power fluctuations that can affect the wavelength of the UV radiation and reduce the effectiveness of the UV disinfection. UV disinfection is highly effective at inactivating microorganisms if the solution is properly filtered and exposed to a sufficient amount of UV radiation. In accordance with the present teachings, the solution is filtered to 0.5 microns, irradiated with a 150 W, medium-pressure UV bulb 72, and circulated through the UV disinfection at a flow-rate of about 90 gal/min.

In a preferred embodiment, the disinfection system 50 also includes a check valve 58 and a flow meter 68 positioned before and after the filtration system 60, respectively, and a flow switch 78 for controlling the UV system 70 in response to the flow rate of the solution 16. The check valve 58 is designed for fluid to flow through in only one direction and is positioned before the pump 52 to ensure the system remains primed once the pump motor is turned off without allowing the solution 16 to reverse flow backward into the chamber 12. A ½" Schedule 80 ball valve can be attached to the side port of the check valve 58 as a convenient way to release the solution 16 within the system into a bucket or other container for spill-free filter servicing and maintenance.

The flow meter 68 is a precision 2" flow meter calibrated to +/−2 gallons per minute accuracy and also functions as a check valve once the pump motor is turned off. The flow meter 68 is positioned after the filtration system 60 and before the UV system 70 because of its dual functioning capability. While the system is pumping, the flow can be easily determined by reading the meter. Once the flow diminishes 10 to 15 gallons per minute below the standard operating rate, it is time to service the filters. While the pump is off, the flow meter 68 acts as a check valve that enables the system to remain primed without allowing the solution 16 to continue flowing forward into the chamber 12. A ½" Schedule 80 ball valve can be attached to the side port of the flow meter 68 as a convenient way to release the solution 16 within the system into a bucket for spill-free filter servicing and maintenance.

The flow switch 78 increases the systems efficiency by continually monitoring the deviations from optimum flow rates. Since it is designed to respond to flow only, (independent of line pressure, temperature, and environment), the flow switch 78 is plumbed in-line before the UV system 70 so that during emergency conditions (line breakage, pump failure, incorrect valve opening or closing) it signals the system of a malfunction and switches the electrical current to the UV light 74 off. When the flow rate surpasses the minimum threshold, it switches the electrical current to the UV light 74 on. The flow switch 78 is a safeguard to protect the chamber 12 and the building it is occupied within from the potential of a fire to develop due to excessive heat generated by operating the UV bulb 74 without liquid flowing through the system.

The disinfection system 50 also includes an ozone injection system 80. The ozone injection system 80 includes a 4 g/hr ozone generator 82 coupled to an ozone injector valve 84 that injects the ozone gas into the solution 16. In the preferred embodiment, the system 80 also includes a water trap 86 for preventing fluid from entering the ozone generator 80. The UV system 70 should be sufficient to inactivate any pathogens in the solution 16. However, UV disinfection does not remove the dissolved organic compounds or chemical contaminants in the solution (such as from perfumes or other personal care products). The ozone system 80 breaks down (oxidizes) these compounds and also acts as a secondary disinfectant for killing any micro-organisms still remaining after UV disinfection. This combination of UV and ozone disinfection is as effective as chlorine disinfection but creates a much safer environment without any harmful chemical by-products.

Optionally, the disinfection system 50 may also include a peristaltic pump 90 coupled to a residual insert injector 92 for injecting a chemical residual into the solution 16. The residual injector 92 may be combined with the ozone injector 84 to form one double injector. As discussed above, a chemical residual is unnecessary and undesirable for this isolation system since the solution 16 is disinfected between every use. However, the peristaltic pump 90 and injector 92 can be included in the system 50 in case a chemical residual is required by law. The isolation system 10 described herein is currently undergoing testing by the NSF (National Sanitation Foundation) to obtain certification that it complies with NSF standards without any chemical residual.

After disinfection, the processed solution 16 is returned to the chamber 12 and then cycled through the disinfection system 50 again for a total of at least five cycles. In the preferred embodiment, all pipes and fittings for connecting the chamber 12 and the various parts of the disinfection system 50 are Schedule 80 PVC plastic certified NSF-PW or NSF-61. As described above, inside the chamber 12, the solution 16 is only in contact with the non-toxic PVC liner 40 and the Schedule 80 vertical slot suction fittings 54. The entire system is therefore fully potable.

The disinfection system 50 is designed to be operated when the chamber 12 is not being used. The solution should be disinfected before each and every use. During a complete disinfection process, the entire volume of solution 16 should be processed through the disinfection system 50 at a rate of approximately 90 gal/min to achieve 3-log kill. A chamber 12 holding 250 gallons of solution should therefore be disinfected for about 10 minutes between each use.

The isolation system 10 should also include an air disinfecting filtration system 94 (such as air disinfecting systems designed for use in surgical clean rooms) for disinfecting and filtering the air within the chamber 12 and killing any airborne pathogens. In the preferred embodiment, the system 10 also includes an oxygen (O2) concentrator 96 (a 5 L O2 concentrator is used in the illustrative embodiment) for injecting extra oxygen into the air supply. The air disinfection system 94 and oxygen concentrator 96 operate in conjunction to provide a continual supply of clean, oxygen-enriched air for the user to breathe while floating. A first air vent 98 couples the enriched air into the chamber 12 and a second air vent 100 allows air to exit the chamber 12. The air vents 98 and 100 each include a 0.5" ball valve sticking out of the bottom port of a 1.5" Schedule 80 PVC tee to release any built-up liquid from trapped condensation.

Thus, the present invention has been described herein with reference to a particular embodiment for a particular application. In relationship to the isolation chamber, in accordance with the present teachings, an improved method of disinfection is taught using UV radiation with ozone injection. Ozone has a short half-life and leaves substantially no toxic byproducts. Verification of disinfection can be accomplished by monitoring the dissolved ozone, which can be determined accurately utilizing a dissolved ozone sensor system.

Those having ordinary skill in the art and access to the present teachings will recognize additional modifications, applications and embodiments within the scope thereof.

It is therefore intended by the appended claims to cover any and all such applications, modifications and embodiments within the scope of the present invention.

Accordingly,

What is claimed is:

1. An isolation system comprising:

a chamber for providing a lightless and soundproofed environment and containing a solution for supporting a user in a state of floatation;

a disinfection system for disinfecting said solution, said disinfection system including a filtration system, an ultraviolet disinfection system and an ozone injection system; and at least one turbulent water intake hydraulically coupled to said pump, said intake including a vertical slot suction fitting submerged to take in said solution to remove fluid at various depths around a 360 degree periphery.

2. The system of claim 1 wherein said solution has a density to provide a buoyancy that effectively counters a floater's specific gravity to bring the floater close to an experience of total weightlessness.

3. The system of claim 2 wherein said solution is a saturated solution of approximately 1000 pounds of USP grade magnesium sulfate for every 250 gallons of water.

4. The system of claim 1 wherein said pump circulates said solution at a flow rate of approximately 90 gallons per minute.

5. The system of claim 4 wherein said ultraviolet disinfection system includes a 150 Watt, medium-pressure ultraviolet bulb positioned to irradiate said solution.

6. The system of claim 5 wherein said ultraviolet disinfection system further includes ballast for regulating electrical current flow to said ultraviolet bulb.

7. The system of claim 1 wherein said disinfection system further includes a flow switch for controlling electrical current supplied to said ultraviolet system in response to a flow rate of said solution.

8. The system of claim 1 wherein said filtration system further includes a 0.5-micron filter.

9. The system of claim 8 wherein said filtration system further includes first and second pre-filters.

10. The system of claim 1 wherein said ozone injection system includes a 4 grams per hour ozone generator.

11. The system of claim 10 wherein said ozone injection system further includes a valve for injecting ozone from said generator into said solution.

12. The system of claim 1 wherein said isolation system further includes an air disinfecting system for disinfecting air within said chamber.

13. The system of claim 12 wherein said isolation system further includes an oxygen concentrator for adding oxygen gas into said chamber.

14. The system of claim 1 wherein said chamber is formed from interlocking, foam-insulated panels.

15. The system of claim 14 wherein said panels are lined with a potable liner that holds the solution.

16. The system of claim 1 wherein said isolation system further includes one or more heating elements and at least one sensor for maintaining said solution at a predetermined temperature matching a skin temperature of the user.

17. A method for filtering an isolation chamber for providing a lightless and soundproofed environment containing a solution sufficiently dense to support a user in a state of floatation including the steps of:

removing a user from the chamber;

circulating said solution through a disinfection system at a predetermined flow rate with a pump and at least one turbulent water intakes hydraulically coupled thereto, each intake including a vertical slot suction fitting submerged to take in said solution to remove fluid at various depths around a 360 degree periphery;

filtering said solution with a filtration system;

exposing said solution to ultraviolet light and then injecting ozone into said solution, whereby said solution is disinfected without chemicals.

* * * * *